(12) United States Patent
Kohler et al.

(10) Patent No.: US 8,496,587 B2
(45) Date of Patent: Jul. 30, 2013

(54) THERAPY SYSTEM FOR DEPOSITING ENERGY

(75) Inventors: Max Oskar Kohler, Finland (FI); Teuvo Vaara, Veikkola (FI); Shunmugavelu Sokka, Brighton, NY (US); Gosta Jakob Ehnholm, Helsinki (FI)

(73) Assignee: Koninklijke Philips N.V., Eindhoven (NL)

( * ) Notice: Subject to any disclaimer, the term of this patent is extended or adjusted under 35 U.S.C. 154(b) by 4 days.

(21) Appl. No.: 13/061,566

(22) PCT Filed: Sep. 3, 2009

(86) PCT No.: PCT/IB2009/053848
§ 371 (c)(1),
(2), (4) Date: Mar. 1, 2011

(87) PCT Pub. No.: WO2010/029474
PCT Pub. Date: Mar. 18, 2010

(65) Prior Publication Data
US 2011/0152730 A1    Jun. 23, 2011

Related U.S. Application Data

(60) Provisional application No. 61/095,367, filed on Sep. 9, 2008.

(51) Int. Cl.
*A61B 8/00*    (2006.01)

(52) U.S. Cl.
USPC ............................................. 600/439; 600/411

(58) Field of Classification Search
USPC .................... 600/407–469; 601/2–4
See application file for complete search history.

(56) References Cited

U.S. PATENT DOCUMENTS

| | | | | |
|---|---|---|---|---|
| 4,951,688 | A * | 8/1990 | Keren | 607/2 |
| 5,792,070 | A * | 8/1998 | Kauphusman et al. | 600/549 |
| 6,419,635 | B1 * | 7/2002 | Hedengren et al. | 600/549 |
| 6,500,121 | B1 * | 12/2002 | Slayton et al. | 600/439 |
| 6,575,969 | B1 | 6/2003 | Rittman, III et al. | |
| 6,589,174 | B1 * | 7/2003 | Chopra et al. | 600/439 |
| 6,916,290 | B2 * | 7/2005 | Hedengren et al. | 600/549 |
| 7,367,944 | B2 * | 5/2008 | Rosemberg et al. | 600/439 |
| 7,799,019 | B2 * | 9/2010 | Turovskiy et al. | 606/33 |
| 8,012,148 | B2 * | 9/2011 | Turovskiy et al. | 606/33 |

(Continued)

FOREIGN PATENT DOCUMENTS

WO    WO2007047247    4/2007

OTHER PUBLICATIONS

Vanne et al, "MRI Feedback Temperature Control for Focused Ultrasound Surgery", Institute of Physics Publishing, Physics in Medicine and Biology, Phys. Med. Biol. 48 (2003) pp. 31-43.

(Continued)

*Primary Examiner* — Sanjay Cattungal

(57) ABSTRACT

A therapy system includes a therapy module, e.g., a high-intensity-focused ultrasound transmitter, to perform successive deposits of energy in a target zone. The successive deposits being separated by a cool down period. The therapy system further includes a thermometry module, e.g. by a magnetic resonance examination system, configured for thermometry to measure temperature in a measurement field. A control module regulates the cool down period in dependence of the measured off-focus maximum temperature during the energy deposit preceding the cool down period.

3 Claims, 2 Drawing Sheets

U.S. PATENT DOCUMENTS

| | | | |
|---|---|---|---|
| 8,016,757 B2 * | 9/2011 | Kaczkowski et al. | 600/438 |
| 8,226,559 B2 * | 7/2012 | Liu et al. | 600/438 |
| 2002/0099304 A1 * | 7/2002 | Hedengren et al. | 600/549 |
| 2006/0259024 A1 * | 11/2006 | Turovskiy et al. | 606/33 |
| 2009/0182230 A1 * | 7/2009 | Liu et al. | 600/439 |

OTHER PUBLICATIONS

Arora et al., "Control of thermal Therapies with Moving Power Deposition Field", Institute of Physics Publishing, Physics in Medicine and Biology, Phys. Med. Biol. 51 (2006) pp. 1201-1219.

* cited by examiner

THERAPY SYSTEM FOR DEPOSITING ENERGY

BACKGROUND OF THE INVENTION

The invention pertains to a therapy system to deposit energy into a target zone.

Such a therapy system is known from the paper 'Determination of the optimal delay between sonications during focused ultrasound surgery in rabbits by using MR imaging to monitor thermal build-up in vivo' by N. J. McDannold et al. in Radiology 211(1999)419-426.

In this document an in vivo sonication experiment is mentioned in which a system for monitoring ablation of tissue is investigated. This known system monitors the ablation process in that heat damage to tissue in monitored. The known system for monitoring ablation performs monitoring e.g. on the basis of magnetic resonance images. Moreover, the cited document mentions that energy can be delivered as sonications in the form of focused ultrasound waves. Further it is mentioned that closely spaced sonications are delivered that are spaced by an intersonication delay to minimize thermal build-up. That is successive deposits of energy are separated in time by a cool-down period. To minimize this intersonication delay the temperature build-up should be measured during treatment. This temperature information is then used to control the intersonication delay.

The cool down period between successive deposits of energy allows temperature to reduce in a region around the focal region into which the energy is directly deposited. Thus, temperature build-up in the region around the focal region, i.e. the so-called off-focus temperature build-up, is reduced. Thus, the risk is reduced for thermal damage to healthy tissue outside of the focal region.

The therapy system is provided with a thermometry module to measure the temperature in a measurement field. Generally, the measurement field contains the focal region into which the energy is directly deposited. The duration of the cool down period between the successive deposits of energy is controlled on the basis of the measured temperature. In this way it is avoided that the time required for the successive deposits of energy is longer than necessary, while off-focus temperature build-up is avoided.

SUMMARY OF THE INVENTION

An object of the invention is to provide a therapy system which is able to more accurately apply energy into the target zone, in particular to more accurately set the cool down period.

This object is achieved by a therapy system according to the invention comprising a therapy module to perform successive deposits of energy in a target zone, the successive deposits being separated by a cool down period, the therapy system being provided with
- a thermometry module to measure temperature in a measurement field and
- a control module to regulate cool down period in dependence of the measured off-focus maximum temperature during the energy deposit preceding the cool down period.

According to the invention, the cool-down period is set on the basis of the maximum temperature outside the focal region in the preceding energy deposit. This involves a relatively simple measurement of the maximum temperature. Because the duration of the cool-down period is more accurately set in order to initiate the next energy deposit as soon as temperature has sufficiently decreases so that the risk of off-focus temperature build-up is low.

In particular when MR thermometry is employed, a relative measurement of temperature of notably the target zone as well as off-focus region is obtained. That is, temperature is accurately obtained relative to a baseline value at the start of an individual energy deposition. As the cool down period between successive energy depositions has been accurately set already from the first energy deposition, reliable equal baseline temperatures apply for subsequent energy depositions.

One of the insights of the invention is that the temperature build-up of tissue outside of the focal region is dependent on the deposited energy density. Notably this is the case for energy deposition in the form of a focused ultrasound beam. The deposited energy density can be accurately calculated a priori and used to estimate the maximum temperature in the off-focus region. The maximum temperature in the off-focus region is approximately linearly dependent on the deposited energy density, i.e. the ultrasound energy density deposited in the off-focus region. The focal off-focus is formed by a cross-section transverse to the beam-path. The linear dependence appears to be valid when temperature decrease due to diffusion of heat can be neglected in the middle of the off-focus ultrasound cone during heating.

According to a further aspect of the invention a comparatively simple approximation of the duration of the cool-down period is proportional to the square of the maximum temperature the off-focus region reached in the preceding energy deposit. This dependency of the cool-down period on maximum temperature holds very well for when the cross-section of the beam-path of the energy deposit is circular (as for example if the beam-path has the shape of a cone). In other cases, the square relationship would be distorted slightly, but the exact relationship can be recalculated for any beam-path cross-section.

In a particular embodiment of the invention, the therapy module is a high-intensity focused ultrasound emitter. In this embodiment the energy deposit is carried-out by irradiating the target zone with a high-intensity focused ultrasound (HIFU) beam, often indicated as 'sonication'. The HIFU-beam causes local heating of the tissue mainly in the focal region which causes thermal ablation in the focal region. Also slight heating of other regions within the HIFU beam occurs.

In another embodiment of the invention, the therapy module is a micro-wave emitter. In this embodiment the energy deposit is carried-out by irradiating the target zone with microwave irradiation. The microwave radiation causes local heating of the tissue which causes thermal ablation in the focal region, while also heating tissues in off-focus areas slightly.

In another embodiment of the invention, the therapy module is an RF-antenna. In this embodiment the energy is deposited via heat-conduction from the antenna placed in contact with the target zone. The RF-heating causes a local temperature increase which causes thermal ablation around the antenna, and by changing the energy density dependency on the maximum temperature rise all of the aspects outlined above may be employed.

In another embodiment of the invention, the monitoring module may rely on MRI, ultrasound or CT images for therapy monitoring. Any other temperature sensitive imaging modality may also be used.

A further embodiment includes a computer program provided on a data carrier such as a CD-rom disk or a USB memory stick, or the computer program of the invention can be downloaded from a data network such as the world-wide web. When installed in the computer included in a therapy system the therapy system is enabled to operate according to the invention and achieve higher safety of use and more accurate setting of the cool down period.

These and other aspects of the invention will be elucidated with reference to the embodiments described hereinafter and with reference to the accompanying drawing wherein

DETAILED DESCRIPTION OF THE EMBODIMENTS

Figure 1:
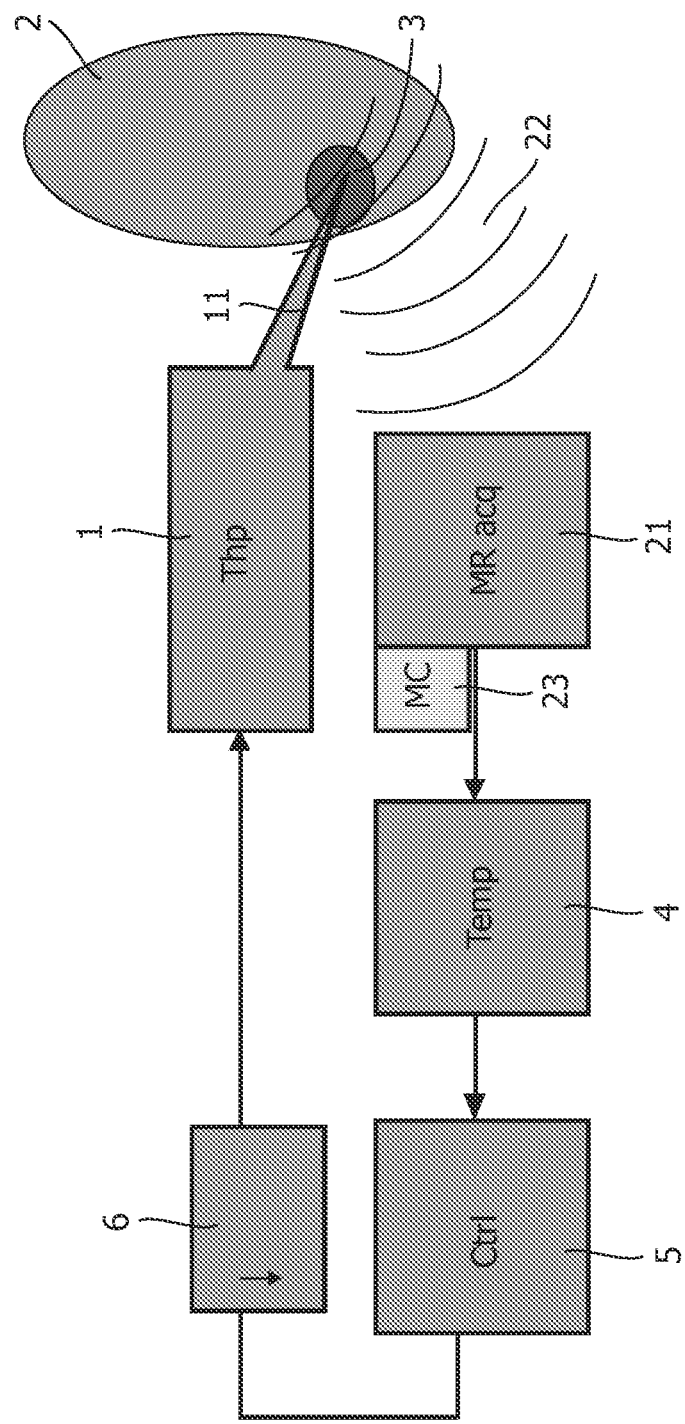
FIG. 1 shows a diagrammatic representation of the therapy system in which the invention is employed.

FIG. 1 shows a diagrammatic representation of the therapy system in which the invention is employed. The therapy unit 1, for example in the form of a high-intensity focused ultrasound (HIFU) unit generates a therapeutic action in the form of a focused ultrasound beam 11. The focused ultrasound beam 11 is accurately directed onto a target zone 2 that includes the actual target 3. For example the target is a tumor in (part of) an organ 2 of the patient to be treated. The HIFU unit 1 is operated so that the focused ultrasound beam 11 moves over the volume of the target zone 2. The ultrasound beam 11 deposits energy in the target zone, causing elevated temperature especially in the tumor. In this way desired parts of the tissue is raised to a level where necrosis of the tissue occurs. Ultimately necrosis occurs in the tissue of the tumor and around it in the target zone once the desired thermal dose or temperature is reached. In particular the thermal dose can be calculated in a simple approximation as $$TD = \int_0^t r^{43-T(\tau)} d\tau,$$

where r=0.25 when T<43° C. and r=0.5 when T>=43° C. A dose limit of 240 equivalent minutes at 43° C. is typically thought to result in necrosis. A modified version of the equation exists that takes the effect of uncertainty into account. In this scope one or several limits (or potentially a lower one) can be checked to ensure that once reached, deposition of energy is stopped. Following temperature only, tells us that necrosis will most probably occur, whereas thermal dose ensures us of it.

For example, necrosis is achieved when the intensity of at the focus of the focused ultrasound beam is about 1600 $Wcm^{-2}$ for a duration of the order of tens of seconds. At this maximum energy level efficient necrosis is achieved without the risk of cavitation. The ultrasound beam can also be used to elevate tissue temperatures to non-necrosis temperature levels. These lower temperatures are useful in hyperthermia type applications.

The temperature distribution of the measurement field is derived from magnetic resonance signals. To this end the patient is placed in a magnetic resonance examination system (not shown) and magnetic resonance signals 22 are generated. The magnetic resonance signals are received by the MR signal acquisition system 21 that is part of the magnetic resonance examination system. The MR signal acquisition system includes RF receiving antennae (coils) and a signal processing system, such as a spectrometer. The acquired magnetic resonance signals are applied to the thermometry module 4 which derives the temperature distribution in the target zone. The phase of the magnetic resonance signals, but also other parameters, depends on temperature. The magnetic resonance signals are spatially encoded by means of encoding magnetic gradient fields, such as read and phase encoding gradients. The spatial resolution of the magnetic resonance signals and the ensuing temperature distribution is at the scale of a millimeter; even sub-millimeter resolution can be obtained where the smallest detail that can de distinguished has a size of a few tenths of a millimeter.

For example if there are several slices in the stack monitoring the temperature, then the measurement field used can advantageously be projected to all parallel slices in the focal-region even though the focal-point trajectory is only in the middle slice of the stack. Because the widest and hottest plane of the typically ellipsoidal heated region may wander towards the transducer during heating, this reduces the risk of the treated region having a larger radius than desired measured from the beam-axis. A measurement field along the beam-axis can also be applied to control that the 240EM dose length does not exceed a maximum length if we have a sagittal plane (which we do). This improves safety considerably.

Off-focus slices (e.g. two of them) can also be added at regions of particular interest, e.g. tissue interfaces where acoustic impedance changes significantly as such regions are prone to off-focus heating. These can be used to automatically detect excessive heating and/or thermal dose in these off-focus areas of interest for any single energy deposit and excessive cumulative heating and/or thermal dose for the entire treatment.

Accurate results in moving tissue are obtained when a motion correction is applied and phase contribution due to motion are separated from phase contributions due to temperature changes. The motion correction can be derived from the magnetic resonance signals, notably by redundant magnetic resonance signals from the central portion of k-space. A motion compensation module 23 is provided to derive the motion correction and apply motion compensation to the magnetic resonance signals. The motion corrected magnetic resonance signals are applied to the thermometry module 4 which derives local temperature distribution of the target zone 3. Alternatively, the motion compensation module 23 can be configured or programmed in software to derive separate the contribution to the phase of magnetic resonance signals due to motion and compute the contribution of the phase due to temperature changes. The local temperature distribution is applied to the control module 5, which controls the therapy module, i.e. the HIFU unit 1 to focus the focused ultrasound beam along a next trajectory. The centre of concentricity can for example be continuously evaluated (e.g. by Gaussian fits or weighted average) to take into account the possibility of the treated (notably heated) region shifting slightly (typically 1-2 voxels or 0.5-5 mm) during treatment due to e.g. spasms or slightly non-uniform heat diffusion.

The therapy system of the invention is provided with a delay module 6 which delays the activation of the therapy module 1. The delay leads to the cool-down period. The delay is set by the control unit on the basis of the measured temperature. The delay unit may be configured to trigger the therapy module. In another embodiment the therapy module is configured to apply regular deposits of energy, e.g. apply regular ultrasound pulses (i.e. sonications). In this embodiment the delay module is configured to interrupt the therapy module. In practice a number of sonications is interrupted or cancelled so as to cause the cool-down period.

Figure 2:
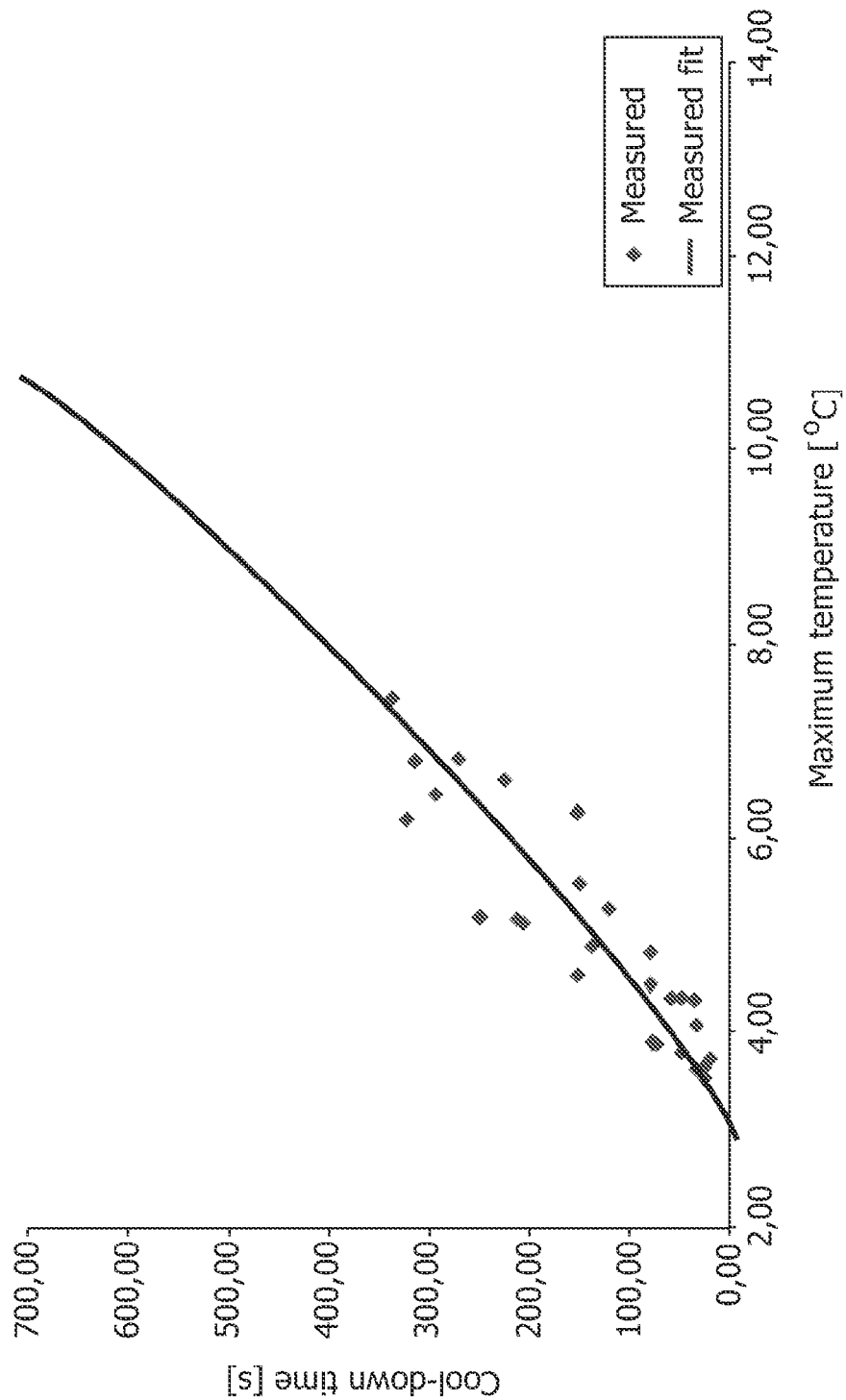
FIG. 2 shows an example of the cool-down time.

FIG. 2 shows an example of the cool-down time to reach within 3° C. of the starting temperature as a function of the maximum near-field temperature. The fit is a square, i.e. quadratic function of the maximum temperature fitted through 3° C. and the R value is 0.90. In these cases the temperature was filtered with a 5×5 voxel median filter (voxel size 2.5×2.5 mm$^2$). Notably, spatial filtering of the measured temperature, e.g. by way of a median filter, improves the signal-to-noise ratio of the temperature measurement. The loss of spatial resolution does not lead to problems since the off-focus heating typically is void of sharp spatial gradients. This data was acquired for a HIFU-therapy module with a circular beam-path cross-section. The fit to 3° C. may be changed to any desired predefined baseline temperature level.

The invention claimed is:

1. A therapy system comprising:
   a therapy module to perform successive deposits of energy in a target zone of a treatment area, the successive deposits being separated by a cool down period;
   a thermometry module configured to measure a maximum temperature in a measurement field located within the treatment area off-focus of the deposited energy; and
   a control module configured to regulate the cool down period in dependence of the measured off-focus maximum temperature during an energy deposit period preceding the cool down period.

2. A therapy system as claimed in claim 1, wherein the therapy module is a high-intensity ultrasound emitter or a micro-wave emitter.

3. A non-transitory computer readable medium embodying a computer program including instructions which, when executed by a processor, configure the processor to perform the acts of:
   successively depositing energy in a target zone of a treatment area, the successive deposits being separated by a cool down period that separates the successive deposits;
   measuring a maximum temperature in a measurement field located within the treatment area off-focus of the deposited energy; and
   regulating the cool down period based on the measured off-focus maximum temperature during an energy deposit period preceding the cool down period.

* * * * *